(12) United States Patent
Gorham et al.

(10) Patent No.: US 7,887,525 B2
(45) Date of Patent: Feb. 15, 2011

(54) COATING COMPOSITION WITH COLOR AND/OR OPTICAL COMPONENTS AND A TAMPON APPLICATOR COATED THEREWITH

(75) Inventors: Patrick Gorham, Wyoming, DE (US); Keith Edgett, Middletown, DE (US); Robert Roman, Leonia, NJ (US); James Wittig, Boonton Township, NJ (US)

(73) Assignee: Playtex Products, Inc., Westport, CT (US)

(*) Notice: Subject to any disclaimer, the term of this patent is extended or adjusted under 35 U.S.C. 154(b) by 0 days.

(21) Appl. No.: 10/877,440

(22) Filed: Jun. 25, 2004

(65) Prior Publication Data

US 2005/0096617 A1    May 5, 2005

Related U.S. Application Data

(60) Provisional application No. 60/482,649, filed on Jun. 26, 2003, provisional application No. 60/502,432, filed on Sep. 12, 2003, provisional application No. 60/536,100, filed on Jan. 13, 2004, provisional application No. 60/566,661, filed on Apr. 30, 2004.

(51) Int. Cl.
*A61F 13/15* (2006.01)
*A61F 13/20* (2006.01)

(52) U.S. Cl. .................... 604/385.17; 604/15

(58) Field of Classification Search .......... 604/11–14, 604/16–18, 385.17, 385.18, 904, 15; 442/59, 442/75
See application file for complete search history.

(56) References Cited

U.S. PATENT DOCUMENTS

| | | | |
|---|---|---|---|
| 2,462,978 A * | 3/1949 | Krchma et al. ............ 423/613 |
| 2,489,502 A | 11/1949 | Ruth | |
| 2,587,717 A | 3/1952 | Fourness | |
| 2,910,482 A | 10/1959 | Gottlieb | |
| 3,071,482 A | 1/1963 | Miller | |
| 3,390,671 A | 7/1968 | Hildebrand | |
| 3,433,225 A | 3/1969 | Voss et al. | |
| 3,628,533 A | 12/1971 | Loyer | |
| 3,717,149 A | 2/1973 | Morane | |
| 3,753,437 A | 8/1973 | Hood et al. | |
| 3,760,808 A | 9/1973 | Bleuer | |
| 3,762,413 A | 10/1973 | Hanke | |
| 3,819,566 A | 6/1974 | Pinsky et al. | |
| 3,830,236 A | 8/1974 | Hanke | |
| 3,861,946 A | 1/1975 | Waitkins et al. | |
| 3,895,634 A | 7/1975 | Berger et al. | |
| 4,027,673 A | 6/1977 | Poncy et al. | |
| 4,038,099 A | 7/1977 | DeLuca, Jr. et al. | |
| 4,077,409 A | 3/1978 | Murray et al. | |
| 4,088,132 A | 5/1978 | Wood et al. | |
| 4,205,995 A | 6/1980 | Wheeler et al. | |
| 4,412,833 A | 11/1983 | Wiegner et al. | |
| 4,453,925 A | 6/1984 | Decker | |
| 4,508,531 A | 4/1985 | Whitehead | |
| 4,534,963 A * | 8/1985 | Gordon ..................... 424/69 |
| 4,543,086 A | 9/1985 | Johnson | |
| 4,650,459 A | 3/1987 | Sheldon | |
| 4,676,773 A | 6/1987 | Sheldon | |
| 4,699,610 A | 10/1987 | Hanano et al. | |
| 4,787,895 A | 11/1988 | Stokes et al. | |
| 4,792,326 A | 12/1988 | Tews | |
| 4,857,044 A | 8/1989 | Lennon | |
| 4,872,933 A | 10/1989 | Tews | |
| 4,900,299 A | 2/1990 | Webb | |
| 4,973,302 A | 11/1990 | Armour et al. | |
| 5,002,526 A | 3/1991 | Herring | |
| 5,087,239 A | 2/1992 | Beastall et al. | |
| 5,153,971 A | 10/1992 | Van Iten | |
| 5,158,535 A | 10/1992 | Paul et al. | |
| 5,267,953 A | 12/1993 | Paul et al. | |
| 5,279,541 A | 1/1994 | Frayman et al. | |
| 5,290,501 A | 3/1994 | Klesius | |
| 5,296,556 A * | 3/1994 | Frihart ..................... 525/420.5 |
| 5,330,421 A | 7/1994 | Tarr et al. | |
| 5,346,468 A | 9/1994 | Campion et al. | |
| 5,348,534 A | 9/1994 | Tomaszewski et al. | |
| 5,350,354 A | 9/1994 | Billmers | |
| 5,376,698 A | 12/1994 | Sipsas et al. | |
| 5,389,067 A | 2/1995 | Rejai | |
| 5,389,068 A | 2/1995 | Keck | |
| 5,393,339 A | 2/1995 | Gerson et al. | |
| 5,395,308 A | 3/1995 | Fox et al. | |
| 5,437,628 A | 8/1995 | Fox et al. | |
| 5,456,749 A | 10/1995 | Iwasa et al. | |
| 5,501,063 A | 3/1996 | Tews et al. | |
| 5,532,350 A | 7/1996 | Cottrell et al. | |
| 5,533,990 A | 7/1996 | Yeo | |
| 5,554,108 A | 9/1996 | Browning et al. | |
| 5,558,631 A | 9/1996 | Campion et al. | |
| 5,569,177 A | 10/1996 | Fox et al. | |
| 5,571,567 A | 11/1996 | Shah | |
| 5,599,293 A | 2/1997 | Orenga et al. | |

(Continued)

*Primary Examiner*—Melanie J Hand
(74) *Attorney, Agent, or Firm*—Ohlandt, Greeley, Ruggiero & Perie, L.L.P.

(57) ABSTRACT

The present invention provides coating composition according to the present invention. The coating composition is a low extractables composition that imparts properties, such as, for example, low friction, high gloss, color and/or pearlescence to a substrate coated with the composition of the present invention. In a preferred embodiment, a tampon applicator includes the coating composition of the present invention.

29 Claims, No Drawings

U.S. PATENT DOCUMENTS

| | | | |
|---|---|---|---|
| 5,601,530 A * | 2/1997 | Nielsen et al. ............... 604/11 |
| 5,643,196 A | 7/1997 | Child et al. |
| 5,683,358 A | 11/1997 | Nielsen et al. |
| 5,693,009 A | 12/1997 | Fox et al. |
| 5,702,553 A | 12/1997 | Iskra et al. |
| 5,709,652 A | 1/1998 | Hagerty |
| 5,738,646 A | 4/1998 | Fox et al. |
| 5,746,710 A | 5/1998 | Nielsen et al. |
| 5,766,145 A | 6/1998 | Fox et al. |
| 5,782,793 A | 7/1998 | Nielsen et al. |
| 5,788,663 A | 8/1998 | Igaue et al. |
| 5,792,096 A | 8/1998 | Rentmeester et al. |
| 5,795,320 A | 8/1998 | Nielsen et al. |
| 5,800,377 A | 9/1998 | Campion et al. |
| 5,804,616 A | 9/1998 | Mowrer et al. |
| 5,817,047 A | 10/1998 | Osborn, III et al. |
| 5,827,214 A | 10/1998 | Fox et al. |
| 5,827,251 A | 10/1998 | Moder et al. |
| 5,873,971 A | 2/1999 | Balzar |
| 5,891,081 A | 4/1999 | McNelis et al. |
| 5,891,127 A | 4/1999 | Moder et al. |
| 5,928,183 A | 7/1999 | Fox et al. |
| 5,931,803 A * | 8/1999 | Jackson ..................... 604/15 |
| 5,954,683 A | 9/1999 | Downs et al. |
| 5,964,741 A | 10/1999 | Moder et al. |
| 5,984,888 A | 11/1999 | Nielsen et al. |
| 6,019,743 A | 2/2000 | Cole et al. |
| 6,024,716 A | 2/2000 | Rejai |
| 6,045,526 A | 4/2000 | Jackson |
| 6,056,714 A | 5/2000 | McNelis et al. |
| 6,068,899 A | 5/2000 | Osborn, III et al. |
| 6,095,998 A | 8/2000 | Osborn, III et al. |
| 6,095,999 A | 8/2000 | Jackson et al. |
| 6,171,426 B1 * | 1/2001 | Blanchard ................. 156/203 |
| 6,179,802 B1 | 1/2001 | Jackson |
| 6,196,988 B1 | 3/2001 | Cole et al. |
| 6,217,542 B1 | 4/2001 | Stevens et al. |
| 6,221,497 B1 | 4/2001 | Roman et al. |
| 6,248,089 B1 | 6/2001 | Porat |
| 6,264,626 B1 * | 7/2001 | Linares et al. ............... 604/15 |
| 6,302,861 B2 | 10/2001 | Tweddell, III et al. |
| 6,322,531 B1 | 11/2001 | Cortese |
| 6,355,011 B2 | 3/2002 | Suga |
| 6,358,223 B1 | 3/2002 | Mackay et al. |
| 6,368,399 B1 | 4/2002 | Aoba et al. |
| 6,368,442 B1 | 4/2002 | Linares et al. |
| 6,383,161 B1 | 5/2002 | Balzar et al. |
| 6,432,075 B1 | 8/2002 | Wada et al. |
| 6,432,076 B1 | 8/2002 | Wada et al. |
| 6,450,985 B1 | 9/2002 | Schoelling et al. |
| 6,450,986 B1 | 9/2002 | Binner et al. |
| 6,458,064 B1 | 10/2002 | Balzar et al. |
| 6,478,764 B1 | 11/2002 | Suga |
| 6,508,966 B1 | 1/2003 | Castro et al. |
| 6,511,451 B1 | 1/2003 | Schoelling et al. |
| 6,524,269 B2 | 2/2003 | McNamara |
| 6,533,748 B2 | 3/2003 | Buzot |
| 6,545,065 B2 | 4/2003 | Solms et al. |
| 6,545,283 B1 | 4/2003 | Williams et al. |
| 6,572,577 B1 | 6/2003 | Binner et al. |
| 6,579,357 B1 * | 6/2003 | Cao ........................ 106/459 |
| 6,610,025 B2 | 8/2003 | Berg et al. |
| 6,648,846 B2 | 11/2003 | Binner et al. |
| 6,730,057 B2 * | 5/2004 | Zhao et al. ................ 604/11 |
| 6,875,264 B2 * | 4/2005 | Zimmermann et al. ...... 106/446 |
| 2002/0042599 A1 | 4/2002 | Zhao et al. |
| 2002/0107305 A1 | 8/2002 | Edler |
| 2002/0107494 A1 | 8/2002 | Williams |
| 2002/0117080 A1 | 8/2002 | Okutsu et al. |
| 2002/0138035 A1 | 9/2002 | Hull, Jr. |
| 2002/0143287 A1 | 10/2002 | Buzot |
| 2002/0183681 A1 * | 12/2002 | Bernard ..................... 604/15 |
| 2003/0028177 A1 | 2/2003 | Berg et al. |
| 2003/0036721 A1 * | 2/2003 | Zhao et al. ................ 604/15 |
| 2003/0040695 A1 | 2/2003 | Zhao et al. |
| 2003/0047118 A1 | 3/2003 | Perry et al. |
| 2003/0073948 A1 | 4/2003 | Binner et al. |
| 2003/0125416 A1 | 7/2003 | Munro et al. |
| 2003/0181844 A1 | 9/2003 | Bernard |

* cited by examiner

COATING COMPOSITION WITH COLOR AND/OR OPTICAL COMPONENTS AND A TAMPON APPLICATOR COATED THEREWITH

RELATED APPLICATIONS

This application claims priority to U.S. Provisional Patent Application Ser. No. 60/482,649 filed on Jun. 26, 2003, U.S. Provisional Patent Application Ser. No. 60/502,432 filed on Sep. 12, 2003, U.S. Provisional Patent Application Ser. No. 60/536,100 filed on Jan. 13, 2004 and U.S. Provisional Patent Application Ser. No. 60/566,661 filed on Apr. 30, 2004.

BACKGROUND OF INVENTION

1. Field of the Invention

The present invention relates to a coating composition and a substrate coated with the coating composition. More particularly, the present invention relates to a coating composition that imparts high gloss, good slip properties, low extractables and appealing aesthetic properties to a substrate coated with the composition. The coated substrate can subsequently be used to form various articles of manufacture that require or would benefit from such properties, including, for example, feminine hygiene products, food-grade products, and the like.

2. Description of Related Art

There exist numerous applications that require a product to possess both highly functional properties in conjunction with highly aesthetic properties. This is especially true with consumer products, where the consumer is not only concerned with how well the particular product functions, but also how the product looks and feels. Another important consideration when making a consumer product is regulatory constraints, which oftentimes restrict the materials from which a product can be formed.

In particular, feminine hygiene products, such as tampons, and food-related products are subject to above-identified constraints, making it extremely difficult to make a product that is highly functional, meets the aesthetic demands of the consumer, and meets any regulatory guidelines.

With regard to tampon applicators, it is widely known that they are generally formed from either a molded thermoplastic material, such as plastic, or a paper laminate, such as cardboard or paperboard.

Molded plastic applicators can be formed with a high degree of surface smoothness, which results in increased comfort during insertion of the tampon applicator. In addition, the molded plastic applicator can be easily modified to include a color, pearlescence, and the like, by modifying the thermoplastic prior to molding. However, plastic tampon applicators, unless certain expensive plastics are used, are neither water dispersible or biodegradable. In an ecology minded society, biodegradability is desired.

To achieve biodegradability, a cardboard or paper laminate applicator is preferred since it delaminates upon saturation with water, thereby facilitating biodegradation. However, a film laminated paper applicator is difficult to form with a perfectly circular cross-section, and the degree of circularity of the laminated paper applicator has been found to further degrade during the tube forming heating stage of the manufacturing process. Moreover, the cardboard applicator must be modified to reduce the coefficient of friction for ease of insertion. In addition, consumers typically find cardboard applicators to be less aesthetically pleasing over their plastic counterparts.

To address both the need for a reduction in the coefficient of friction of the cardboard applicator, some commercially sold cardboard applicators have applied thereto either a separate film laminate bonded by adhesive, or a liquid coating which then solidifies.

A polyester film coating, which has been used on commercially sold tampon applicators, has been found to shrink during the heating cycle of the applicator manufacturing process, causing the distortion of the applicator's shape thereby increasing the ejection force. A cellophane film also shrinks due to the evaporation of water absorbed from the adhesive used to apply it to the applicator. Further, cellophane is usually coated with a water-resistant coating, such as nitrocellulose. Nitrocellulose coating of cellophane is expensive, and requires the use of a volatile organic solvent to apply the coating. The use of such a solvent requires special handling and disposal procedures, all of which further raise manufacturing costs.

Liquid coated paper laminate applicators are known in the art. For example, U.S. Pat. No. 4,412,833 to Weigner et al. is directed to an applicator formed of a high-gloss paper that can be coated with a degradable, dispersible or water soluble polymer, such as a modified polyethylene, polypropylene, polyvinylidene chloride or polyvinyl alcohol. U.S. Pat. No. 4,508,531 to Whitehead provides an applicator with a heat-sensitive coating, such as polyolefin (e.g., polyethylene or polypropylene) or a heat sensitive adhesive.

However, neither the liquid nor film coatings applied to the prior art cardboard tampon applicators described above have permitted the combination of formation of the desired reduction in friction, glossy finish, retention of applicator circularity, and sufficient biodegradability, let alone while further providing enhanced aesthetics to the applicator. Further, some prior art liquid coatings are more expensive, and require the use of organic solvents, leading to increased manufacturing cost and consumer cost.

The present invention overcomes the difficulties in providing additional aesthetic properties to a substrate and/or product without compromising the functional properties of the substrate or product, while still meeting regulatory requirements. This is accomplished by providing a low extractables coating that imparts additional properties such as, for example, low coefficient of friction, high gloss, color, and/or pearlescence to the substrate coated with the composition. As a result, a highly functional product having enhanced aesthetics is efficiently produced without compromising any of the desired functional properties.

SUMMARY OF THE INVENTION

It is an object of the present invention to provide a coating composition for use on both paper-based and plastic-based substrates.

It is another object of the present invention to provide such a coating composition that has low extractables.

It is still another object of the present invention to provide such a coating composition that imparts a low coefficient of friction to a coated substrate.

It is yet another object of the present invention to provide such a coating composition that imparts one or more aesthetic properties to a coated substrate.

It is another object of the present invention to provide such a coating composition that imparts one or more aesthetic properties to a coated substrate without compromising the functional properties of the coated substrate.

It is a further object of the present invention to provide a tampon applicator having such a coating composition.

It is still another object of the present invention to provide a process for forming a substrate having such a coating composition.

It is yet another object of the present invention to provide a process for forming a tampon applicator having such a coating composition.

These and other objects and advantages of the present invention will be appreciated from a coating composition according to the present invention. The coating composition is a low extractables composition that imparts properties, such as, for example, low friction, high gloss, color and/or pearlescence to a substrate coated with the composition of the present invention. In a preferred embodiment, a tampon applicator includes the coating composition of the present invention. In another preferred embodiment, the tampon applicator is made from a paper-based or cardboard material.

DETAILED DESCRIPTION OF THE INVENTION

The coating composition of the present invention should provide a substrate with at least two physical properties including, but not limited to, low friction, low extractables, toughness, high gloss, biodegradability, color, and pearlescence. In addition, the coating composition should have good adhesion to both paper-based materials and plastic-based materials. The coating can be used on any substrate or product that would benefit from having the above-stated properties. Such substrates and/or products include, but are not limited to, tampons or tampon applicators, packaging, food-related packaging, infant feeding products, and labels.

The coating composition according to the present invention includes a base component for the coating composition. Suitable base components for use in the present invention include, but are not limited to, resin, wax or any combinations thereof. Suitable resin for use in the present invention includes, but is not limited to, epoxy, acrylic, urethane, polyester, silicone, UV curable epoxy, UV curable acrylic, electron beam curable epoxy, electron beam curable acrylic, UV curable silicone, electron beam curable silicone, thermally curable silicone, modified resins such as styrenated acrylic, epoxy acrylate, polyester acrylate, polyester, vinyl ester, vinyl ether, vinyl chloride, polyvinyl alcohol, polyvinyl acetate, and any modifications or combinations thereof.

In one embodiment of the present invention, the resin is an epoxy resin. In a preferred embodiment, the resin is a UV curable epoxy blend. By way of example, U.S. Pat. No. 5,931,803, incorporated by reference herein in its entirety, discloses UV curable epoxy blends suitable for use in the present invention. Also, by way of example, U.S. Pat. No. 6,221,497, incorporated by reference herein in its entirety, discloses UV curable epoxy blends suitable for use in the coating composition of the present invention.

The coating composition of the present invention also includes one or more optical components added to the resin, which impart aesthetic properties to the coating composition without compromising the ultimate functionality of the coating composition. Such components may include, but are not limited to, mica, $TiO_2$-coated mica, iron oxide coated mica, bismuth oxychloride, holographic material, pearlescence material, reflective material, glitter, metallic effect pigment, interference pigment, liquid crystal effect material, or any combinations thereof. The above optical components may be natural or synthetic in origin. Preferably, the optical component used in the coating composition of the present invention is mica, $TiO_2$-coated mica, iron oxide coated mica, bismuth oxychloride, or any combination thereof.

When present, the one or more optical components are included in the coating composition in an amount about 1 weight percent (wt. %) to about 70 wt. %, based on the total weight of the coating composition. More preferably, the one or more optical components are present in an amount about 2 wt. % to about 25 wt. %, and most preferably about 5 wt. % to about 15 wt. %.

In one embodiment of the present invention the optical component used in the coating composition of the present invention is bismuth oxychloride. When bismuth oxychloride is used, it preferably has a particle size of about 8 to about 11 microns and is present in the coating composition in an amount about 5 wt. % to about 50 wt. %. More preferably, the bismuth oxychloride has a particle size of about 9 microns to about 10 microns and is present in an amount about 25 wt. % to about 35 wt. %.

For example, it has been found that the use of bismuth oxychloride, when carefully homogenized in the composition results in an improved dispersion. This improved dispersion imparts improved rub-resistance characteristics to the coating. In addition, the homogenized bismuth oxychloride particles also result in improved luster or brilliance characteristics in the coating composition, which results in improved appearance properties.

In another embodiment of the present invention the optical component used in the coating composition of the present invention is mica, $TiO_2$-coated mica, iron-oxide coated mica, or any combinations thereof. Preferably, the optical component is $TiO_2$-coated mica. Examples of suitable mica components include, but are not limited to, components sold by Engelhard under various tradenames including MAGNAPEARL, MEARLIN, MEARLITE, and LUMINA, and Merck's EM Chemicals division, which sells AFFLAIR.

Mica based pigments are irregularly shaped mica platelets that may be coated with titanium dioxide or iron oxide. When added to a coating composition according to the present invention, they produce a variety of pearlescent effects including a white lustrous to sparkly appearance, an interference or flop color that changes appearance with the viewing angle, or metallic silver and gold effects. $TiO_2$-coated mica may be made using both anatase and rutile grades of titanium dioxide. The rutile grade is preferred, as it produces a higher luster and better whiteness.

When mica, and particularly $TiO_2$-coated mica is used, it preferably has a particle size of about 2 microns to about 150 microns and is present in the coating composition in an amount about 1 wt. % to about 60 wt. %. More preferably, the mica has a particle size of about 2 microns to about 10 microns and is present in an amount about 2 wt. % to about 20 wt. %, and more preferably about 5 wt. % to about 15 wt. %.

The coating composition of the present invention may include one or more color components either alone or in combination with one or more optical components to selectively impart a color to the coating composition. Suitable color components may include, but are not limited to, colorants, dyes, inorganic pigments, organic pigments, or any combinations thereof. Preferably, one or more pigments are included in the resin to impart color. Suitable pigment may include, but is not limited to, titanium dioxide, white titanium dioxide, iron oxide, red iron oxide, orange iron oxide, white zinc sulfide, aluminum powder, bronze powder, Red Lake C, phthalocyanine green, phthalocyanine blue, phthalocyanine red, diarylide yellow, quinacridone red, rhodamine red, lithol rubine red, napthol red, neozapon red, carbizole violet, carbon black, or any combinations thereof.

When present, the one or more color components are included in the resin in an amount about 0.001 wt. % to about 5 wt. %. Preferably, the one or more color components are present in an amount about 0.01 wt. % to about 3 wt. %, and more preferably about 0.5 wt. % to about 1 wt. %.

To form the coating composition of the present invention, the one or more color components are blended into the resin material. Special care must be taken when formulating the coating composition of the present invention to avoid adding the one or more color components in such an amount or manner that ultimately compromises the desired and/or required physical properties of the final coating composition.

Additionally, special consideration must be given to the selection of the color components used in the present invention, as they must be compatible with the resin material, and especially the curable resin material. With respect to the curable resins, color components having amine or acid functionality should be avoided since these functional groups can interfere with the curing and/or shelf stability of the resin resulting in an undesirable composition.

In an embodiment of the present invention, the coating composition includes wax as the base component for the composition. One or more color components are included in the coating composition in an amount about 0.001 wt. % to about 5 wt. %, based on the total weight of the composition. Optionally, one or more optical components may be included in this coating composition in an amount about 5 wt. % to about 50 wt. %, based on the total weight of the composition. Preferably, the resulting wax-based, colored coating composition is applied to a tampon applicator.

It has been unexpectedly found that the unique blend of resin material with the one or more select color components results in a coating, that when applied to a substrate, demonstrates comparable and/or superior properties to a similar coating without the select color components. Moreover, the composition of the present invention also exhibits similar properties, both functional and aesthetic, to those of plastic. This is especially important on cardboard tampon applicators coated with the coating composition of the present invention.

It has also been surprisingly found that the coating composition of the present invention exhibits an enhanced gloss. As a result, the coating composition has an enhanced visual appearance. Moreover, by way of example, when the coating composition is applied to a cardboard tampon applicator, the enhanced gloss gives the cardboard applicator a plastic-like appearance. The gloss, as measured at a 60° angle pursuant to ASTM D523, attributed to the coating composition of the present invention is in the range between about 30 to about 95, and preferably about 30 to about 60.

By way of example, the gloss, as measured at a 60° angle pursuant to ASTM D523, is in the magnitude of about 50 to 53, as demonstrated by the data set forth below in Table 1. Examples 1 through 3 represent coating compositions with a color component applied to a paper substrate according to the present invention.

TABLE 1

Gloss Measurements

| Example | Coating Color | Gloss @ 60° Angle |
| --- | --- | --- |
| Comparative Example 1 | Clear Coat | 41.5 |
| Example 1 | Purple | 52.33 |
| Example 2 | Red | 52.16 |
| Example 3 | Blue | 51.66 |

Another important attribute of the coating composition of the present invention is that it possesses excellent colorfastness. The term colorfastness, as used herein, is the resistance of a material to change in any of its color characteristics, to transfer any of its colorant(s) to adjacent materials, or both, as a result of the exposure of the material to any environment that might be encountered during the processing, testing, storage, or use of the material. It is believed that the coating composition of the present invention would experience little to no color transfer, when tested pursuant to a test such as, for example, AATCC Test Method 8-1981.

Another attribute of the coating composition of the present invention is an increase in heat resistance. This is important as the coating composition will remain heat stable during production, shipment, storage and use.

Once formulated, the coating composition can be applied to any desired substrate by any process known in the art of coating substrates. Suitable processes include, but are not limited to, spraying, laminating, topcoating, dipping, printing, melting, extrusion or any combinations thereof.

In one particularly preferred embodiment, the coating composition is formulated and applied to a paper-based or cardboard tampon applicator. This coating composition includes a UV curable epoxy resin and less than about 1 wt. % of at least one color pigment that is compatible with the UV curable epoxy resin. This coating provides the tampon applicator with not only a low coefficient of friction and high gloss, but also a colored, plastic-like appearance. Moreover, the coating has low extractables. Notably, 21 CFR §175.300 requires that the extractables in tampons not exceed 0.5 mg/in$^2$. As demonstrated in Table 2 below, the tampons having the coating of the present invention all have extractables levels below the 0.5 mg/in$^2$ limit.

With respect to Table 2, Comparative Examples 2 through 5 represent cardboard tampons having a clear coat UV curable epoxy resin coating without an optical component and a color component. The white color is the underlying cardboard layer seen through the clear coating. Examples 4 through 9 represent cardboard tampon applicators coated with a coating composition with a UV curable epoxy resin and color component, according to the present invention. Examples 10 through 20 represent cardboard tampon applicators coated with a coating composition including a UV curable epoxy resin, bismuth oxychloride, and a color pigment, according to the present invention.

Consistent with the procedures outlined in 21 CFR §175.300, to measure the extractables, the coated paper is tested in accordance with Condition of Use E., room temperature filled and stored using a distilled water extractant at 120° F. for 24 hours. The results are reported in milligrams per square inch.

TABLE 2

| | Extractables | | |
| --- | --- | --- | --- |
| Example | Coating Color | Coat Wt. (#/Ream) | Qty. Extracted (mg/sq in) |
| Comparative 2 | White 15% | 4.00 | 0.183 |
| Comparative 3 | White | 4.00 | 0.262 |
| Comparative 4 | White 30% | 3.70 | 0.258 |
| Comparative 5 | White 20% | 4.00 | 0.248 |
| Example 4 | Pink | 4.25 | 0.290 |
| Example 5 | Pink | 4.15 | 0.270 |
| Example 6 | Purple | 4.25 | 0.310 |

TABLE 2-continued

Extractables

| Example | Coating Color | Coat Wt. (#/Ream) | Qty. Extracted (mg/sq in) |
|---|---|---|---|
| Example 7 | Purple | 4.15 | 0.280 |
| Example 8 | Blue | 4.25 | 0.300 |
| Example 9 | Blue | 4.15 | 0.280 |
| Example 10 | Silver | 4.00 | 0.373 |
| Example 11 | Silver 30% | 3.70 | 0.265 |
| Example 12 | Lavender | 4.00 | 0.342 |
| Example 13 | Lavender 30% | 4.00 | 0.277 |
| Example 14 | Pink 30% | 3.90 | 0.303 |
| Example 15 | Green | 3.83 | 0.413 |
| Example 16 | Green 30% | 3.81 | 0.275 |
| Example 17 | Blue | 3.85 | 0.417 |
| Example 18 | Blue 15% | 4.02 | 0.295 |
| Example 19 | Blue 20% | 3.80 | 0.323 |
| Example 20 | Blue 30% | 3.85 | 0.282 |

As is evident from the data in Table 2, the tampons coated with the coating composition according to the present invention exhibit the necessary low extractables below 0.5 mg/in$^2$.

Moreover, other key attributes of a coating composition, such as tensile strength, tensile modulus, and elongation, are not compromised by the coating composition according to the present invention, contrary to conventional wisdom. This is reflected in the data set forth below in Table 3 and Table 4.

Typically, one would expect the addition of components, such as color components and or optical components, to adversely effect the properties of the coating composition. Comparative Example 6 is represented by a tampon having a clear UV curable epoxy coating without color component. Example 21 represents a tampon applicator coated with a coating composition having a UV curable epoxy resin and color component, according to the present invention.

TABLE 3

| | Tensile Strength (psi) | Tensile Modulus at 1% Deflection (psi) | Elongation (%) |
|---|---|---|---|
| Comparative Example 6 | 6900 | 203000 | 3.6 |
| Example 21 | 6500 | 225000 | 2.8 |

As demonstrated by this data, there is an increase in modulus which helps to improve the stiffness of the coated paper with out compromising tensile strength or toughness, as opposed to the prior art coating, which excludes the color component.

The data set forth below in Table 4 further demonstrates that the coating compositions of the present invention can impart various aesthetic properties to a substrate coated with the coating compositions, without comprising key physical properties of the substrate.

TABLE 4

| Test | Tampon Applicator with Clear Coating | Tampon Applicator with Coating Having Color Component | Tampon Applicator with Coating Having Color Component and Bismuth Oxychloride | Tampon Applicator with Coating Having Color Component and Mica | Testing Method |
|---|---|---|---|---|---|
| Film Modulus | 200,000 psi | 200,000 psi | 225,000 psi | 210,000 psi | ASTM D882-02 - Instron At 1% Deflection |
| Film Elongation | 3.8% | 3.8% | 2.8% | 3.2% | ASTM D882-02 |
| Film Tensile Strength | 6,900 psi | 6,900 psi | 6,500 psi | 6,300 psi | ASTM D882-02 |
| Film Adhesion to Substrate | Pass | Pass | Pass | Pass | ASTM D3359-02 |
| Gloss @ 60% angle | 52 | 55 | 32 | 36 | ASTM D2457-03 |
| Sutherland Rub | Pass | Pass | Pass | Pass | ASTM D5264-98 200 Rubs with a 4 lb. Weight Face to face |
| Static Friction | 0.206 | 0.210 | 0.211 | 0.155 | ASTM D1894-01 |
| Kinetic Friction | 0.169 | 0.171 | 0.139 | 0.118 | ASTM D1894-01 |

As is evident in the data set forth above, a tampon applicator with a coating composition with color component exhibits a higher gloss and comparable coefficient of friction to a tampon applicator having a clear coat. In addition, a tampon applicator with a coating having color component and optical component, such as bismuth oxychloride and/or mica, exhibits a notable decrease in coefficient of friction over a tampon with a clear coat. Particularly, kinetic coefficient of friction measurements between about 0.1 to about 0.2 are achieved by coating compositions according to the present invention.

Once formulated, the coating composition can be applied to any desired substrate by any process known in the art of coating substrates. Suitable processes include, but are not limited to, spraying, topcoating, roll coating, dipping, printing, melting, extrusion, hot melt extrusion, slot die, knife, gravure, offset gravure, flexo, letterpress, offset and litho, screening, or any combinations thereof.

In the case of a cardboard tampon applicator, the coating composition is preferably applied to an outer surface of a base paper layer. This coated paper layer is then cut to the appropriate size and adhered to the inner plies of paper that make up the base applicator structure. The applicator is preferably spiral wound; however, it could be formed as a convolute tube.

The coating composition can be applied to the entire applicator, or to any portion of the applicator desired. This may include any portion of the applicator, including any portion of the barrel and/or plunger.

To achieve the desired properties of the coating composition on the tampon applicator, it has been found that the coating should be applied in a thickness of about 2 microns to about 50 microns. Preferably, the coating has a thickness of about 3 microns to about 6 microns.

Additional coating compositions are disclosed in co-pending provisional patent applications bearing Ser. Nos. 60/482,649 filed on Jun. 26, 2003; 60/502,432 filed on Sep. 12, 2003; and 60/536,100 filed on Jan. 13, 2004, all of which are incorporated in their entirety by reference herein.

Other modifications of the present invention will be obvious to those skilled in the art in the foregoing teachings. Moreover, while the present invention has been described with reference to specific embodiments and particular details thereof, it is not intended that these details be construed as limiting the scope of the invention.

We claim:

1. A multi-layered cardboard tampon applicator comprising a barrel and a plunger, wherein said barrel and said plunger each have a coating comprising:
   one or more color components present in an amount about 0.001 wt. % to about 5 wt. %, based on the total weight of the coating, wherein said one or more color components are one or more pigments selected from the group consisting of titanium dioxide, white titanium dioxide, iron oxide, red iron oxide, orange iron oxide, white zinc sulfide, aluminum powder, bronze powder, Red Lake C, phthalocyanine green, phthalocyanine blue, phthalocyanine red, diarylide yellow, quinacridone red, rhodamine red, lithol rubine red, napthol red, neozapon red, carbizole violet, carbon black, and any combinations thereof; and
   one or more optical components present in an amount about 1 wt. % to about 70 wt. %, based on the total weight of the coating, wherein said one or more optical components are selected from the group consisting of mica, $TiO_2$-coated mica, iron oxide coated mica, bismuth oxychloride, and any combination thereof;
   wherein said barrel and said plunger each have at least an inner ply and an outer ply of paper.

2. The tampon applicator of claim 1, wherein said coating composition further comprises a base component selected from the group consisting of resin, wax, and any combinations thereof.

3. The tampon applicator of claim 2, wherein said base component is resin selected from the group consisting of epoxy, acrylic, urethane, polyester, silicone, UV curable epoxy, UV curable acrylic, electron beam curable epoxy, electron beam curable acrylic, UV curable silicone, electron beam curable silicone, thermally curable silicone, modified resins such as styrenated acrylic, epoxy acrylate, polyester acrylate, polyester, vinyl ester, vinyl ether, vinyl chloride, polyvinyl alcohol, polyvinyl acetate, and any combinations thereof.

4. The tampon applicator of claim 3, wherein said base component is an UV curable epoxy.

5. The tampon applicator of claim 1, wherein said one or more optical components are natural or synthetic in origin.

6. The tampon applicator of claim 1, wherein said one or more optical components are present in said coating composition in an amount about 2 wt. % to about 25 wt. %, based on the total weight of said coating composition.

7. The tampon applicator of claim 1, wherein said one or more optical components are present in said coating composition in an amount about 5 wt. % to about 15 wt. %, based on the total weight of said coating composition.

8. The tampon applicator of claim 1, wherein said one or more optical components is bismuth oxychloride.

9. The tampon applicator of claim 8, wherein said bismuth oxychloride has a particle size of about 8 to about 11 microns and is present in said coating composition in an amount about 5 wt. % to about 50 wt. %.

10. The tampon applicator of claim 1, wherein said one or more optical components is mica, $TiO_2$-coated mica, iron-oxide coated mica, and any combinations thereof.

11. The tampon applicator of claim 1, wherein said one or more optical components is $TiO_2$-coated mica.

12. The tampon applicator of claim 11, wherein said $TiO_2$-coated mica has a particle size of about 2 microns to about 150 microns and is present in said coating composition in an amount about 1 wt. % to about 60 wt %, based on the total weight of said composition.

13. The tampon applicator of claim 1, wherein said one or more color components are present in an amount 0.01 wt. % to about 3 wt. %, based on the total weight of the composition.

14. The tampon applicator of claim 1, wherein said one or more color components are present in an amount about 0.5 wt. % to about 1 wt. %, based on the total weight of the composition.

15. The tampon applicator of claim 1, wherein said coating composition is applied to said tampon applicator in a thickness of about 2 microns to about 50 microns.

16. The tampon applicator of claim 1, wherein said coating composition is applied to said tampon applicator in a thickness of about 3 microns to about 6 microns.

17. The tampon applicator of claim 1, wherein said tampon applicator with said coating composition has a kinetic coefficient of friction between about 0.1 to about 0.2.

18. The tampon applicator of claim 1, wherein said tampon applicator with said coating composition has an extractables less than 0.5 mg/in$^2$.

19. The tampon applicator of claim 1, wherein said tampon applicator with said coating composition has a film modulus greater than about 200,000 psi.

20. The tampon applicator of claim 1, wherein said tampon applicator with said coating composition has a gloss at a 60° angle between about 30 to about 95.

21. The tampon applicator of claim 1, wherein said tampon applicator with said coating composition has a gloss at a 60° angle between about 30 to about 60.

22. A multi-layered cardboard tampon applicator comprising a barrel and a plunger, wherein said barrel and said plunger each have a coating comprising:

a wax base component;

one or more color components present in said coating composition in an amount about 0.001 wt. % to about 5 wt. %, based on the total weight of the composition, and selected from the group consisting of titanium dioxide, white titanium dioxide, iron oxide, red iron oxide, orange iron oxide, white zinc sulfide, aluminum powder, bronze powder, Red Lake C, phthalocyanine green, phthalocyanine blue, phthalocyanine red, diarylide yellow, quinacridone red, rhodamine red, lithol rubine red, napthol red, neozapon red, carbizole violet, carbon black, and any combinations thereof; and one or more optical components present in said coating composition in an amount about 5 wt. % to about 50 wt. %, based on the total weight of the composition, and selected from the group consisting of mica, $TiO_2$-coated mica, iron oxide coated mica, bismuth oxychloride, and any combinations thereof, wherein said barrel and said plunger each have at least an inner ply and an outer ply of paper.

23. The tampon applicator of claim 22, wherein said coating composition is applied to said tampon applicator in a thickness of about 2 microns to about 50 microns.

24. The tampon applicator of claim 1, wherein said applicator is a spiral wound or a convolute applicator.

25. The tampon applicator of claim 22, wherein said applicator is a spiral wound or a convolute applicator.

26. The tampon applicator of claim 1, further comprising a UV curable epoxy resin.

27. The tampon applicator of claim 26, wherein said one or more color components are a pigment in an amount less than about 1 wt. % based on the total weight of the coating.

28. The tampon applicator of claim 22, wherein said one or more color components are present in said coating composition in an amount about 0.01 wt. % to about 3 wt. %, based on the total weight of the composition.

29. The tampon applicator of claim 22, wherein said one or more color components are present in said coating composition in an amount about 0.5 wt. % to about 1 wt. %, based on the total weight of the composition.

* * * * *